United States Patent [19]
Alpern

[11] Patent Number: 5,271,495
[45] Date of Patent: Dec. 21, 1993

[54] OVAL WRAP SUTURE PACKAGE WITH ROTARY WHEEL

[75] Inventor: Marvin Alpern, Glen Ridge, N.J.

[73] Assignee: Ethicon, Inc., Somerville, N.J.

[21] Appl. No.: 53,968

[22] Filed: Apr. 26, 1993

Related U.S. Application Data

[63] Continuation of Ser. No. 861,677, Apr. 1, 1992, abandoned.

[51] Int. Cl.⁵ .............................................. A61B 17/06
[52] U.S. Cl. ..................................... 206/63.3; 206/380
[58] Field of Search ................. 206/63.3, 339, 380; 242/137, 137.1, 138, 170, 171; 606/145–147

[56] References Cited

U.S. PATENT DOCUMENTS

| | | | |
|---|---|---|---|
| 3,545,608 | 12/1970 | Berger et al. | 206/63.3 |
| 3,901,244 | 8/1975 | Schweizer | 206/63.3 X |
| 4,084,692 | 4/1978 | Bilweis | 206/63.3 X |
| 4,961,498 | 10/1990 | Kalinski et al. | |
| 4,967,902 | 11/1990 | Sobel et al. | 206/63.3 |
| 5,052,551 | 10/1991 | Cerwin et al. | 206/63.3 |
| 5,056,658 | 10/1991 | Sobel et al. | 206/63.3 |
| 5,131,534 | 7/1992 | Brown et al. | 206/63.3 |

*Primary Examiner*—Bryon P. Gehman

[57] ABSTRACT

A package for a suture and surgical needle. The package defines an oval channel for winding the suture. An inner needle park retains the needle. A wheel is rotatably mounted to one end of the package, forming one end of the suture channel. The suture package retains the suture in the channel.

59 Claims, 5 Drawing Sheets

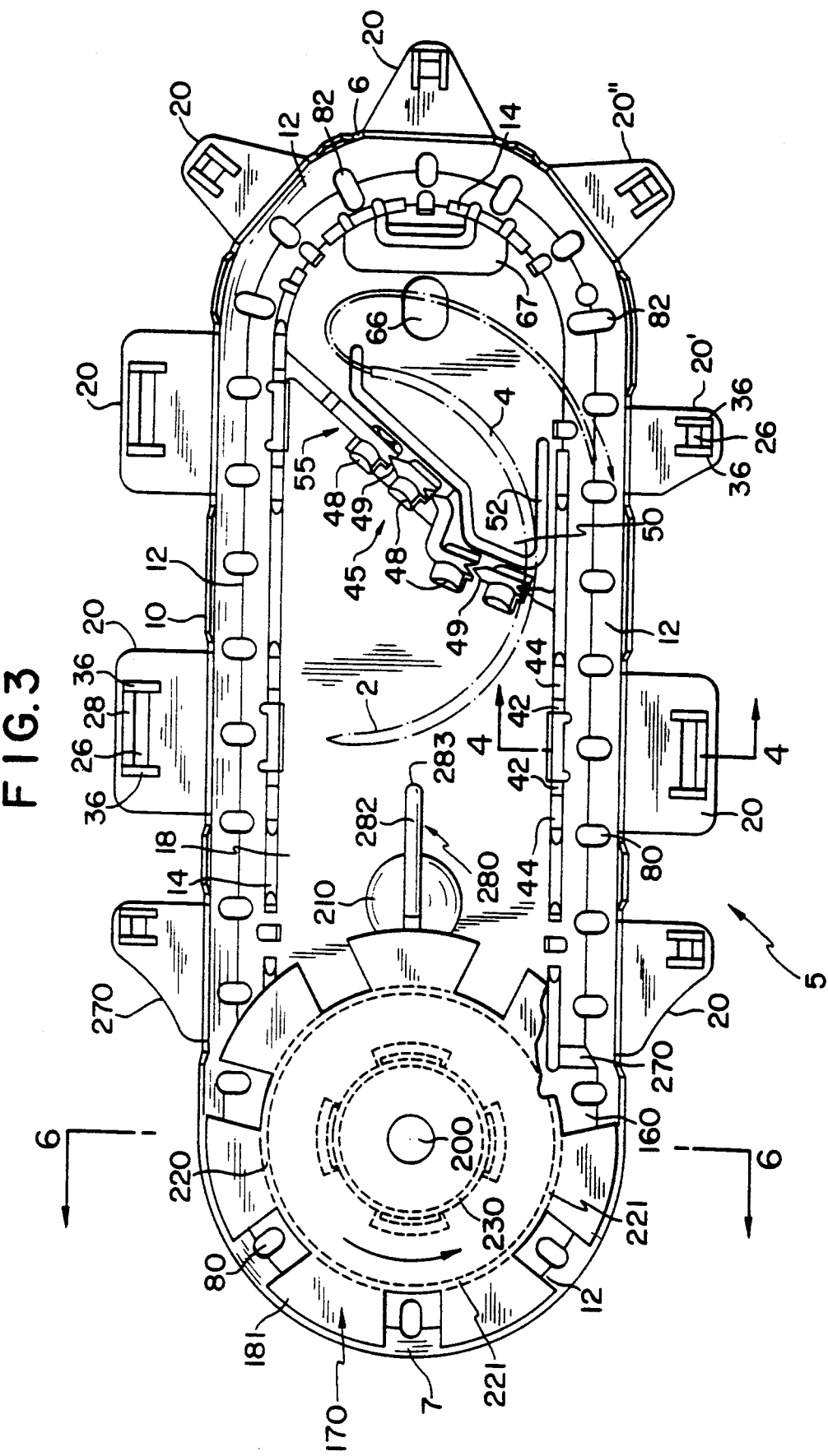

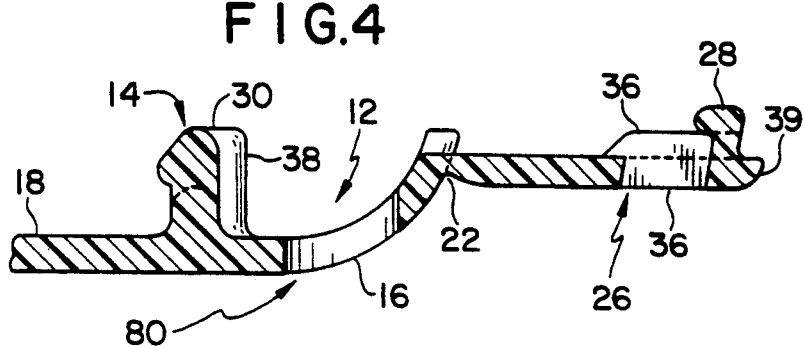
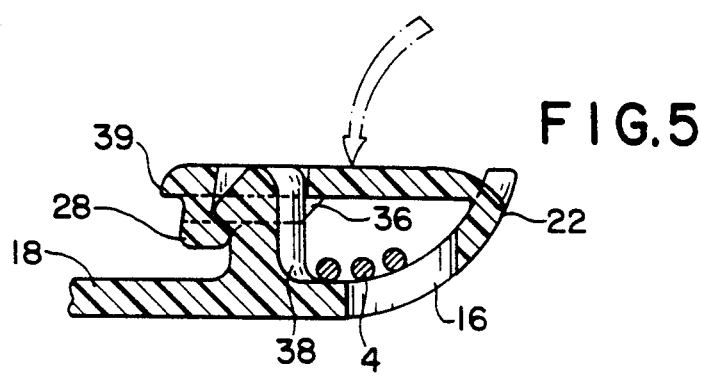
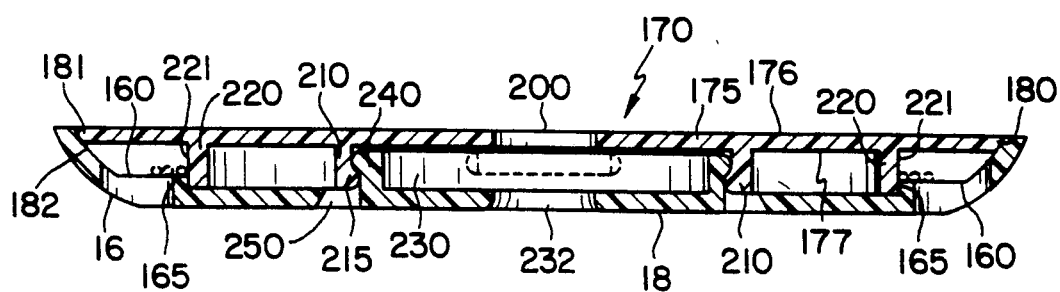

OVAL WRAP SUTURE PACKAGE WITH ROTARY WHEEL

This is a continuation of application Ser. No. 861,677, filed Apr. 1, 1992, now abandoned.

FIELD OF THE INVENTION

The field of art to which this invention relates is packages for holding sutures and sutures with attached needles.

BACKGROUND ART

Sutures and sutures having surgical needles attached have typically been packaged in single use containers or packages. The packages retain the suture and needle during shipping and storage. In addition to protecting a suture and needle, it is desirable that a suture package facilitate rapid, easy removal by the health care professional.

Problems which can occur with suture packages include binding and snagging of the suture in the package when rapid removal is attempted. In addition, the loops of the suture contained in the package may become entangled. It is also known that monofilament suture materials such as catgut, polydiaxanone and the like tend to develop a "memory" when stored over time. The "memory" phenomena can also cause problems such as binding and snagging.

It is desirable for sutures to be substantially straight when withdrawn from a suture package. The suture should not have loops, twists, kinks or bends which may hinder or interfere with the suturing procedure. Oval wrap suture packages have been developed which provide a means for packaging a suture in a compact package, while allowing the suture to have a substantially straight configuration when withdrawn from the package.

U.S. Pat. No. 4,961,498 discloses an oval wrap suture package. The molded two-piece suture package encloses and defines an oval channel in which sutures may be wound. An opening in the channel is provided allowing a suture to be withdrawn while preventing entrapment.

U.S. Pat. No. 4,967,902 discloses an oval one-piece needle and suture holder in which an oval-shaped channel is formed for retention of a suture. The holder contains a needle park. The oval channel includes gently rounded end sections, eliminating tight bends or curves which induce undesirable suture "memory".

There have been previous attempts to address the problem of suture binding and snagging in oval wrap suture packages.

U.S. Pat. No. 5,052,551 discloses an oval wrap suture package with unequal end radii. The package defines an oval channel with opposing semicircular end sections wherein one end section has a larger area than the other.

There is a constant search in this art for improved suture packages having improved suture release characteristics.

SUMMARY OF THIS INVENTION

Therefore, it is an object of the present invention to provide a suture package which has improved suture release characteristics. It is yet another object of the present invention to provide improved suture packages which are easily manufactured in high volume quantities.

In accordance with the principles of the present invention, a needle and suture holder package is described in which an oval-shaped channel is formed for retention of the suture. The needle and suture holder package has a base and a rotatably attached wheel means. One end of the suture exits the oval channel toward the center of the oval and is attached to a surgical needle located in the center of the oval. The oval channel includes a first rounded end section, two opposed longitudinal side sections and a second opposed rounded end section having a rotatably attached wheel means, eliminating a capstan effect. The rotatably attached Wheel means forms an inner periphery about said channel in said second end section. The end sections connect the side sections to form the oval channel. The oval shaped channel is formed with an open side, to which are attached a plurality of hinged doors. After the suture is wound in the open channel, the wheel means is rotatably attached to the base and the doors are folded over the open side of the channel and are locked in place to retain the suture within the channel. In a preferred embodiment, the wheel means comprises at least one wheel. To afford ease of winding the suture, the bottom of the channel is perforated for the application of a vacuum to the channel during suture winding. Also disclosed is a needle park means for retaining a needle in the center of the package. In a preferred embodiment, the needle park means is backed by a relief flap to enable the needle to be conveniently grasped by forceps.

Other features and advantages of the invention will become more apparent from the following description and accompanying drawings.

BRIEF DESCRIPTION OF THE DRAWINGS

FIG. 3 is a plan view of the suture package of FIG. 1;

FIG. 4 is a partial cross-sectional view of the oval channel showing a hinged door in the open position;

FIG. 5 is a partial cross-sectional view of the oval channel showing a hinged door in the closed and locked position;

FIG. 6 is a cross sectional view of the wheel end of the suture package;

DESCRIPTION OF THE PREFERRED EMBODIMENTS

U.S. Pat. No. 5,052,551, U.S. Pat. No. 4,967,902, and U.S. patent application No. 751,039 filed on Aug. 28, 1991 are incorporated herein by reference.

Figure 1:
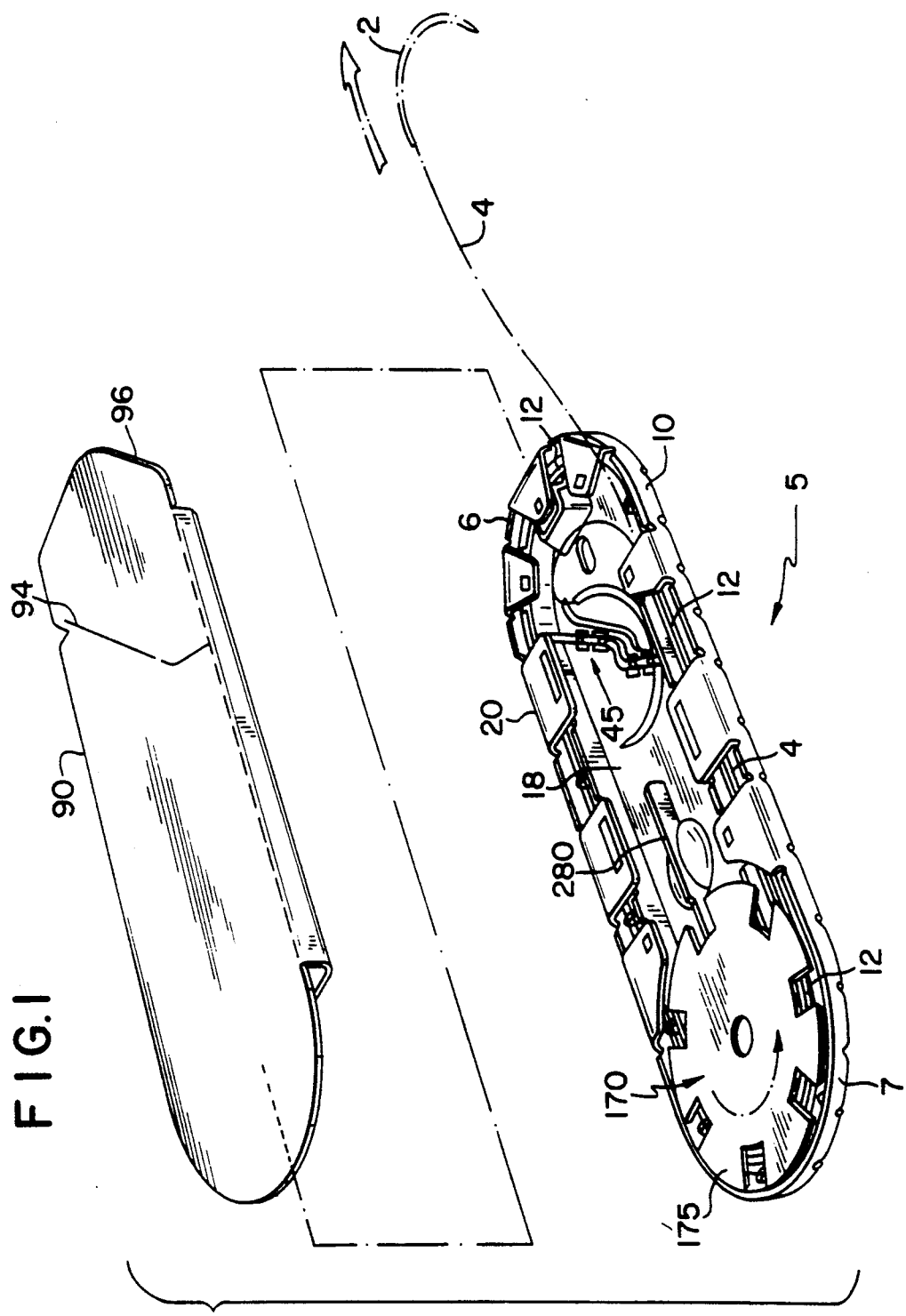
FIG. 1 illustrates a perspective view of a suture package constructed in accordance with the principles of the present invention.
Figure 2:
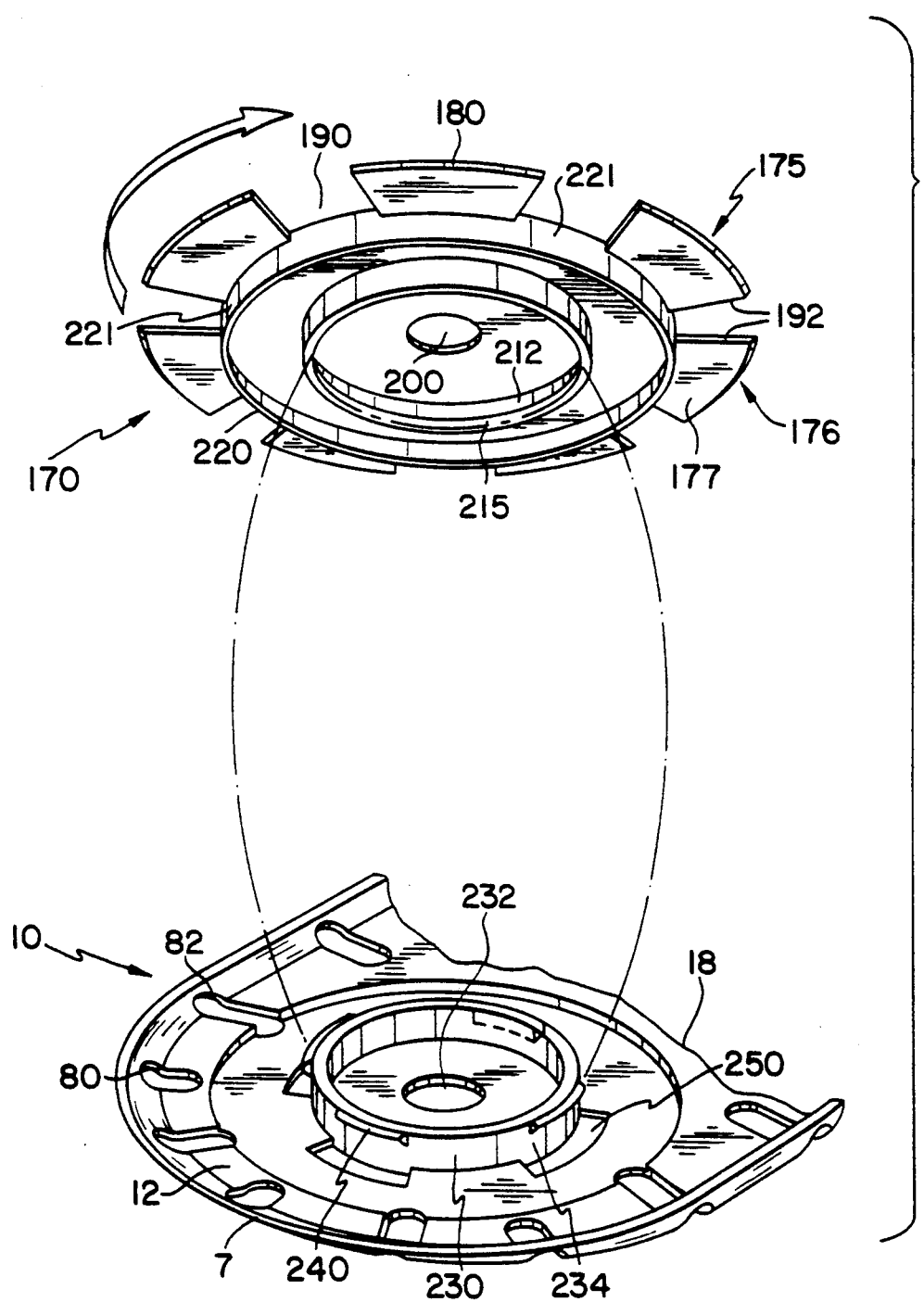
FIG. 2 is a perspective view of a wheel means and a partial perspective view of the wheel end of the suture package of the present invention.

Referring first to FIGS. 1, 2 and 3, a suture package 5 of the present invention is shown in perspective and plan views, respectively. The package 5 may be formed of any surgically compatible polymeric materials such as polyester plastic, polyethylene, polyvinyl chloride (PVC), polypropylene, or polystyrene, and combinations thereof and the like. If desired, a sufficient amount of at least one conventional lubricating material may be added to the polymeric material effective to provide decreased frictional resistance to the withdrawal of a suture 4 from package 5. Conventional lubricants include oleamides, organosilicones and the like.

The package 5 is seen to have a base 10 which has a central floor area 18. Central floor area 18 is surrounded by an outer oval channel 12 having two opposing longitudinal sections connected by one semicircular end section 6 at one end and a semicircular section 7 at the other end about the periphery of wheel 170. The term semicircular as used herein is defined to include the arc of a circle as well as any curved, rounded or arcuate shape, and geometric shapes which would approximate an arcuate or curved shape such as a section of a polygon having a large number of sides. The longitudinal and vertical axes of package 5 are defined to mean herein the major and minor axes, respectively, of the package 5. The channel 12 is defined by an inner wall 14 which extends upwardly from the floor area 18 along the longitudinal sections and semicircular end 6, and is also defined by wheel 170 along the other curved end 7. Portions of the door locking means are formed at intervals about the inner wall 14. The bottom and outer periphery of the channel 12 are defined by a curved section 16 of the package 5, which extends outwardly from the inner wall 14 at the level of the floor 18 and which also extends from the outer support ring 220 of the wheel 170 at the level of the floor channel 160 and curves upwardly to approximately the elevation of the top of inner wall 14, and the top 176 of wheel 170. Attached at the outer periphery of the curved section 16 opposite the inner wall 14 are a plurality of hinged doors 20. The doors 20 are hinged at an elevation which is slightly below the uppermost elevation of the outer periphery of the curved section 16 and the inner wall 14 so that, when the doors 20 are folded over the channel and latched in place, the upper surfaces of the doors will align with the upper elevation of the outer periphery and inner wall 14. Formed in each door 20 is a portion of the door locking means, including a latch opening 26 bounded by a door latch projection 28 and two fins 36, which are described in further detail below.

As can be seen in FIG. 3, located inside the oval channel is a needle park 45 for holding needles which includes members 48. Needle park 45 will be described in further detail below. Adjacent the needle park 45 is a relief flap 50 defined by a cutout 52. A portion of the inner wall 14 is eliminated in the vicinity of the needle park to form a vent 40 in the inner wall 14 through which the suture of the needle accesses the channel 12 between doors 20' and 20". The bottom of the channel 12 which is formed by the curved section 16 is periodically perforated by holes 80 and 82 around the periphery of the channel.

Referring to FIG. 1, FIG. 2 and FIG. 3, a hub ring 230 having an outer wall 234 is seen to extend upwardly from the floor 18 of the suture package 10 at the semicircular end section 7 of the package 5. Circular hub hole 232 is concentric with hub ring 230 and extends through floor 18. Hub ring 230 has arcuate tab fins 240 extending outwardly from the top of the outer wall 234 of hub ring 230. The arcuate fins 240 are circumferentially located along the outer wall 234 of hub ring 230 along the longitudinal and vertical axes of the hub ring 230 and are centered at 90°, 180°, 270°, and 360° with reference to the longitudinal axis of hub ring 230. The longitudinal and vertical axes of hub ring 230 correspond to the major and minor axes of the package 5. Arcuate holes 250 through the floor 18 are similarly configured circumferentially about hub ring 230.

Referring to FIG. 1, FIG. 2, FIG. 3, and FIG. 6, it is seen that the wheel means in a preferred embodiment comprises at least one wheel, e.g., wheel 170. The wheel 170 has a disc 175 having an upper side 176, a bottom side 177, and a central, concentric circular hole 200 extending through disc 175. An outer concentric support ring 220 extends downwardly from the bottom side 177 of the disc 175. An inner concentric hub support ring 210 extends downwardly from the bottom 177 of disc 175. The hub support ring 210 has inner wall 212. Extending inwardly from the bottom of inner wall 212 is continuous inwardly extending tab fin 215. The disc 170 has a rim 180. A plurality of rim openings 190 through the disc 175 extend inwardly from the rim 180 in a radial manner with the sides 192 of openings 190 extending inwardly in a chordal manner.

Referring to FIG. 1, FIG. 2, and FIG. 3, it can be seen that the wheel 170 is rotatably mounted to the floor 18 by concentrically mounting the hub support ring 210 extending from the bottom side 177 of the wheel 170 onto the hub ring 230 such that the center of the wheel 170 is in axial alignment with the hub ring 230. The hub support ring 210 is sized to have a larger inner diameter than the outer diameter of the hub ring 230. The tab fins 240 on the hub ring 230 engage the tab fin 215 on the hub support ring 210, allowing the wheel 170 to freely rotate about the hub ring 230, while also retaining the wheel 170 by preventing axial or lateral displacement. It will be further observed that the rim 180 has top circumferential edge 181 around top side 176 and lower circumferential edge 182 around bottom side 177. Rim 180 is angulated inwardly and downwardly from top circumferential edge 181 to bottom circumferential edge 182.

Referring to FIG. 3 and FIG. 6, the section of the channel 12 defined by the outer side 221 of outer support ring 220 and the curved section 16 has a raised floor channel section 160 extending from floor 18 to form step 165. The diameter of outer support ring 220 is sized to provide a clearance sufficient to allow rotation of the wheel 170 while effectively preventing a suture 4 from slipping between outer side 221 and step 165. The clearance is typically about 0.005 inches to about 0.010 inches, preferably about 0.010 inches between the step 165 and the outer side 221. The raised floor channel 160 is seen to transition downwardly to the level of floor 18 through ramps 270 located in channel 12 on either side of wheel 170.

Referring to FIG. 1, an ellipsoidal member 290 is seen to extend outwardly from floor 18 along the longitudinal axis of package 5. A central fin 280 extends upwardly from floor 18 through ellipsoidal member 290. The central fin 280 has a pair of opposed, substantially parallel, longitudinal side walls 282, and a pair of arcuate ends 283. The central fin 280 and the ellipsoid member 290 are disposed adjacent to the rim 180 of wheel 170. The purpose of the fin 280 is to provide structural rigidity to the base 10.

FIG. 4 and FIG. 5 are a partial cross-sectional views of the package of FIG. 1 and FIG. 3 showing in enlargement a hinged door 20 and the channel 12. The hinge 22 of the door 20 is attached to the outer periphery of the channel 12 at an elevation which is just below the uppermost elevation of the channel on either side of the hinge 22 so that the door 20 will be flush with the top of the channel 12 when it is closed. The door locking means 24 includes a door latch opening 26 and a door latch projection 28. An overhang 39 is formed at the edge of the door. A fin 36 is located at each end of the door latch opening 26.

Referring concurrently to FIG. 4 and FIG. 5., a latch post 30 is formed in the inner wall 14 opposite the hinge door 20. A pair of standoffs 38 are formed along the inner wall at either end of the latch post location as shown also in FIG. 1. Extending from the latch post 30 toward the inside of the package (i.e., over the floor 18) is a latch post projection 32.

When the door 20 is closed and latched to retain a suture 4 within the channel 12 it has the cross-sectional appearance as shown in FIG. 5. The top of the latch post 30 engages the door latch opening 26 and the door latch projection 28 hooks around the latch post projection 32 to lock the door in the closed position. The door 20 is prevented from unlatching in the presence of lateral compression by the abutment of the edge 34 of the opening 26 against the edges of the standoffs 38, which prevents unhooking of the two projections. When the door is closed, the sides of the door rest on the edges 44, shown in FIG. 3 and FIG. 5, locating the upper surface of the door flush with the top of the inner wall 14. The fins 36 at either end of the opening 26 engage the openings 42 at either end of the latch post 30. The fins 36 and the standoffs 38 serve to prevent the suture from binding or becoming entrapped in the door locking means. As FIG. 4 and FIG. 5 illustrate, the curved fins 36 and the standoffs 38 cause the suture to be located away from and to bridge the engaged door opening 26 and latch post 30, preventing the suture 4 from becoming caught between these two members, either during closure of the door 20 or during withdrawal of the suture 4 from the channel 12.

Referring to FIGS. 1 and 3, the needle park 45 of the package 5 can be seen. The needle park means 45 may comprise any conventional needle means wherein a plurality of needles is held in a member having openings, slits or slots therein for receiving and holding the needles. It is particularly preferred to use a needle park means 45 comprising a plurality of members 48 extending from the base 18. The members 48 are located on base 18 to form a wall 55. The members 48 are separated from each other by gaps 49. A needle 2 is inserted into a gap 49 and is compressively retained by members 48. Members 48 extend from base 18 in a "living-hinge" arrangement and are capable of deflection to accommodate a variety of needle widths in the gap 49. Needle park means are described in U.S. patent application No. 751,039 which is incorporated by reference.

Referring to FIG. 1 and FIG. 3, an assembled package 5 with a needle 2 and suture 4 is shown. A paper cover 90 is also seen in FIG. 1. The package is easily assembled by placing the package 5 on an assembly platform with a number of upwardly extending pins. Two of the pins are aligned to extend upward through holes 66 and hub hole 232 in the center of the package to retain the package in its assembly position on the platform. Eight other pins extend upward and are aligned to pass through the holes 82 of the channel (see FIG. 3). The assembly platform is open beneath the remaining channel holes 80 and a vacuum source below the platform draws air through the holes 80. With the package 5 so emplaced, the needle 2 is located in the needle park 45 as shown in the drawing, and the suture 4 is looped about the pin extending through hole 66 then downward through the vent 40 and into the channel 12. The suture is then wound in a clockwise direction around the pins which extend through the channel holes 82. It may be seen in FIG. 2 and FIG. 3 that the holes 82 extend inward toward the center of the package by a greater dimension than holes 80. This allows location of the extending pins close to the inner wall 14. When the suture 4 is wound around the pins and the pins then are withdrawn from the holes 82, the suture 4 will be loosely positioned in the center of channel 12, since the pins serve to keep the suture 4 away from the inner wall 14 in the channel 12 during winding by the dimension of the thickness of the pins. The pins also serve to locate the suture 4 away from the location of outer side wall 221 of outer support ring 220 so that the wheel 170 can be mounted without binding the suture 4. As the suture 4 is wound around the pins, the flow of air through the holes 80 will draw the suture 4 down into the channel 12. When the end, or "tail" of the suture 4 is reached, the flow of air will likewise draw the tail of the suture 4 into the channel 12. With the suture completely wound in the channel 12 the doors 20 are folded closed and latched to the latch posts 30 of the inner wall 14 and the wheel 170 is rotatably mounted to hub ring 210. The pins are then withdrawn from the holes 66, 232, and 80.

The optional paper cover 90, which is seen to comprise a sleeve-like member, may then be placed about the package 5 to fully protect the suture 4 and needle 2 from any further contact during final assembly of the package 5. The cover 90 includes a scored tear line 94 along which the cover will preferentially tear when it is grasped at the tear corner 96 for opening. In an alternate embodiment (not shown), the cover 90 may comprise a flat member having a plurality of perforated push-out tabs. These tabs are located so as to be in alignment with the closed doors 20. When the tabs are pressed downward, the outer edges of the tabs snap under the overhanging edges 39 of the doors 20 with which they are aligned, thereby retaining the cover in place on the package 5.

The enclosed suture package 5 is then ready for optional final overwrap packaging, which typically comprises hermetically sealing the package in a conventional foil overwrap using conventional sealing and packaging techniques. Next, the sealed suture package 5 is sterilized using conventional sterilization techniques including autoclaving, radiation sterilization using cobalt-60, and the like.

When the package 5 is to be opened, the user grasps the tear corner 96 of the package 5 and tears the overwrap and cover downward, causing the cover 90 to open along the scored tear line 94. This reveals that portion of the package to the right of the needle park 45, with the point of the needle 2 still protected by the cover 90 to the left of the needle park 45. The user then grasps the needle 2 with a forceps. Since the needle 5 is resting flush with the floor 18 of the package 5, making it difficult to securely grasp the needle 2 with the tip of the forceps, the relief flap 50 is provided. As the user presses the tip of the forceps against the relief flap 50 the flap 50 will give way and bend away from the needle 2, thereby enabling the user to pass the tip of the forceps beyond the needle 2. The needle 2 may then be securely grasped in the tip of the forceps and removed from the needle park 45.

Moreover, when the package 5 is enclosed in a foil overwrap, the silver of the foil which backs the package 5 behind the needle 4 can blend with the silvery needle 4, causing the needle 4 to be difficult to distinguish from this reflective background. The relief flap 50 obviates this problem by presenting a contrasting background behind the needle 4. The polymeric package 5 can be tinted or colored a milky white or some other contrasting color, using conventional dyes or pigments approved for medical use, which will highlight the needle in front of the relief flap 50. The flap 50 also covers the foil overwrap located behind the flap 50. This contrasting background thus makes it easier to clearly see fine gauge needles in the package.

FIG. 3 shows a ramp 67 formed to the right of the relief flap 50 location. The ramp 67 is also shown in FIG. 1. The purpose of the ramp 67 is to guide the needle 2 barrel up and out of the inner wall 14 of the channel 12 at the curved end of the package.

Figure 7:
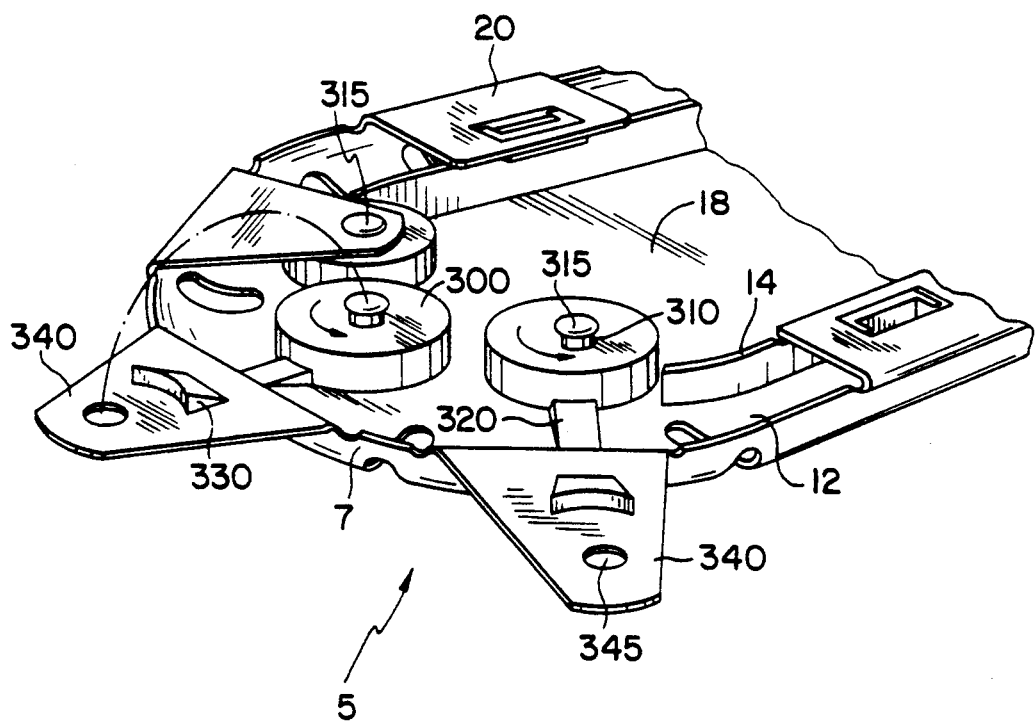
FIG. 7 is a partial perspective view of an alternate embodiment of the wheel means of the suture package of the present invention.

Referring to FIG. 7, an alternate embodiment of the wheel means of the present invention can be seen. Three wheels 300 are seen rotatably mounted to posts 310, however, any number of wheels may be used sufficient to provide an arcuate or semicircular end channel 12 in the end 7 of package 5. The wheels 300 are seen to be discs having central mounting holes 305. The posts 310 act as mounting posts and axles about which wheels 300 rotate. The posts 310 are seen to have swaged tops 315 to retain the wheels 300 and door members 340. The wheels 300 are seen to be positioned in a semicircular manner about the end 7 of the floor 18 to conform to the semicircular channel 12. Ramps 320 prevent the suture 4 from binding between the wheels 300 and the floor 18. Doors 340 are hingingly attached to the top of outer curved section 16 and are seen to have openings 345 which snap over the tops 315 of posts 310 to secure the wheels 300 on the posts 310. Ramp members 330 are seen to extend from door members 340 to prevent a suture 4 from binding between the door members 340 and wheels 300. Door members 340 are seen to enclose the channel 12 in the same manner as the doors 20. It will be appreciated by those skilled in the art that the wheel means can comprise any combination of rotating elements having substantially round or curved configurations so as to define an inner perimeter for channel 12 in end 7.

In a conventional figure-8 wound suture package, the suture is looped from its point of attachment at the barrel of the needle back toward the point of the needle, where the figure-8 wind is formed. This configuration can cause the needle tip to catch on a loop of the suture and damage the suture. However, in the package of the present invention it can be seen that the suture 4 is looped to the right from the barrel of needle 2 about the hole 66 and down through vent 40. This winding pattern keeps the suture 4 removed to the right of the needle 2 and the needle point. As the needle 2 is lifted from the needle park 45 and the suture 4 is pulled from the channel 12, the suture 4 is kept to the right of and away from the point of needle 2 and any possible damage.

It will be appreciated by those skilled in the art that equivalent locking means may be used to lock doors 20 other than the locking means shown in FIGS. 4 and 5. In an alternate embodiment not shown, the door locking means includes a plurality of posts located around the outer surface of the wall 14 in alignment with the doors 20. The posts are offset from the surface of the wall 14 to provide standoffs for the suture from the wall 14. The door locking means also includes a pair of holes formed in each door 20. When the hinged doors are closed the posts mate in the holes of the doors 20 in a force fit to hold the doors closed. The posts can alternatively be sized to extend through the doors 20, enabling the tips of the posts to be swaged to secure the doors in their closed position.

In yet another embodiment of the present invention (not shown), the doors 20 are eliminated. The channel 12 is enclosed, either wholly or partially, by a flat, paper cover having a plurality of holes about its periphery. Similarly, a plurality of posts extends upward from the top of wall 14. The posts are in alignment with the holes in the paper cover and are engaged by said holes. The ends of the posts which extend through the cover are then softened or swaged to hold the cover in place. The paper cover further includes a cover flap overlying the needle position of the package 5. The cover flap is hinged to the cover at a fold line.

The suture packages 5 of the present invention have many advantages over the suture packages of the prior art. Surprisingly and unexpectedly, the suture packages of the present invention have improved release characteristics when compared to previously known oval channel suture packages. In particular, it is surprising and unexpected that the incidence of "lock-ups" and "re-pulls" is greatly decreased. In this art, the term "lock-up" is used to describe a defect which occurs wherein during the course of removing a suture from a package, the suture suddenly locks up, preventing further removal from the package. A "lock-up" typically results in the suture and needle being unusable, since it is not possible to remove the suture from the package in the health care environment. Lock-ups can be described as catastrophic failures. The term "re-pull" in this art is used to describe a defect which occurs wherein as the health care provider is removing the suture from a package, a sudden seizure of the suture occurs within the package, preventing further removal. However, the suture can be removed by relaxing the suture and re-pulling. In contrast, to "lock-up", a "re-pull" can be remedied by taking the appropriate immediate action.

It is essential that suture packages dispense the suture quickly and efficiently and in a predictable manner. It can be appreciated that, since sutures are used in critical care situations, including operations and the treatment of trauma resulting from accidents, where time is of the essence, it is of the utmost importance that suture "lock-up" or "re-pull" defects be eliminated or minimized.

While not desiring to be held to any particular theory or explanation, it is believed that "lock-up" and "re-pull" in an oval channel suture package are caused by a "capstan" effect. The capstan effect is believed to be caused by an erratically wound suture or by a shifting of the wound suture during shipping and handling. It is believed that the inclusion of wheel means such as a rotatable wheel 170 to form part of the oval channel suture channel 12 of the present invention eliminates or minimizes the capstan effect and the rotation of the wheel 170 prevents the suture 4 from locking about the wheel 170. As mentioned previously, the incidence of "lock-ups" and "re-pulls" in the oval channel suture package 5 of the present invention in comparison to conventional oval channel suture packages is reduced.

Although this invention has been shown and described with respect to detailed embodiments thereof, it will be understood by those skilled in the art that various changes in form and detail thereof may be made without departing from the spirit and scope of the claimed invention.

What is claimed is:

1. A suture package that defines an oval suture winding channel comprising:

two opposed longitudinal sections;
each of a first semicircular end section and a second semicircular end section connecting said longitudinal sections; and,
a suture wound in the suture winding channel
a base; and,
wheel means for assisting dispensing of the suture within the channel from the suture package, said wheel means rotatably attached within the suture package opposite to said first semicircular end section and adjacent to said second semicircular end section, said wheel means defining the inner periphery of the channel in said second semicircular end section.

2. The package of claim 1 further comprising a plurality of door means hingingly attached to said suture winding channel, said door means being closeable to enclose the suture within said suture winding channel.

3. The package of claim 2 further comprising means for locking said door means in their closed position.

4. The suture package of claim 3, wherein said means for locking said door means comprises a latch mechanism located on at least one of said door means and said channel.

5. The suture package of claim 4 wherein said latch mechanism includes an aperture located in said door means and an interlocking post located on said channel.

6. The suture package of claim 5, wherein said door means further includes fin means projecting from said door means or preventing binding of a suture within said latch mechanism.

7. The suture package of claim 5, and further comprising a cover sleeve enclosing said package.

8. The suture package of claim 7, wherein said cover sleeve further includes a scored tear line enabling said cover to preferentially open to reveal a needle location within said package.

9. The suture package of claim 2, wherein said suture winding channel is located about the periphery of a central area of said package, said suture winding channel has an open side, and said door means are hingingly attached at said open side of said channel for closure over said open side of said channel.

10. The suture package of claim 9, wherein said channel further includes an inner wall projecting from the base of said package and standoff means projecting from the inner wall of said channel for bridging sections of said inner wall.

11. The suture package of claim 1, wherein said suture winding channel is located about the periphery of said package and includes an inner wall projecting from the base of said package and wherein said suture package further comprises a central area substantially surrounded by said channel and having a point of access to said suture winding channel.

12. The suture package of claim 11, further comprising a needle park means for holding a needle, said needle park means located in said central area and wherein said point of access allows passage of a suture from said central area into said channel.

13. The suture package of claim 12, further comprising;
a curved needle having a barrel located in said needle park means with the ends of said needle curving away from said point of access; and
the suture attached to the barrel of said curved needle and forming a loop extending from said barrel away from the point of said needle and into said point of access.

14. The suture package of claim 11, wherein each of said longitudinal sections comprises a substantially straight section and wherein said point of access is located in the vicinity of the connection of said first semicircular end section to a substantially straight section.

15. The suture package of claim 11, wherein said point of access comprises an opening in the inner wall of said suture winding channel.

16. The suture package of claim 1, wherein said suture winding channel is located about the periphery of said package and includes an inner wall projecting from the base of said package, and an opposing outer edge, wherein said wheel means comprises a wheel rotatably attached to the base of said package, and wherein said door means are hingingly attached about said outer edge of said channel.

17. The suture package of claim 16, wherein said suture winding channel further includes a curved section extending outward from the base to said outer edge.

18. The suture package of claim 17, wherein said suture winding channel in at least one cross-section comprises a substantially planar inner wall, a planar top wall formed by said door means, and a curved wall connecting said inner and top walls when said door means are closed,
wherein portions of said channel are open intermediate said door means when said door means are closed.

19. The package of claim 1 wherein the wheel means comprises at least one wheel rotatably mounted to the base by wheel attachment means for attaching said wheel means to the base.

20. The suture package of claim 19 wherein the at least one wheel comprises a disc having an upper surface, a bottom surface, and a center, the disc having an outer ring extending downwardly from the bottom surface of the disc for engaging the suture.

21. The suture package of claim 20 wherein the at least one wheel additionally comprises a second, concentric inner ring extending downwardly from the bottom of the disc for rotatably attaching the at least one wheel to the base, said inner ring having locking means for locking the at least one wheel to the base.

22. The suture package of claim 20 wherein the disc extends outwardly to enclose the second semicircular end of the suture channel opposite to the first semicircular end section and adjacent to the at least one wheel.

23. The suture package of claim 20 wherein the at least one wheel comprises a plurality of holes extending through the disc so that the suture contained in the suture package is visible in the channel about the at least one wheel.

24. The suture package of claim 20 wherein said at least one wheel additionally comprises a hole extending through the center of the disc.

25. The suture package of claim 19 wherein said suture channel has a bottom including a raised portion, the raised portion located adjacent to the wheel means.

26. The suture package of claim 25 wherein there is a transition ramp between the base and the raised portion.

27. The suture package of claim 19 wherein the wheel attachment means comprises a hub extending upwardly from the base.

28. The suture package of claim 27 wherein the hub comprises a hub ring extending upwardly from the base for rotatably mounting the at least one wheel, said hub having locking means for locking the at least one wheel in place while allowing rotation about the hub.

29. The suture package of claim 28 wherein the locking means comprises at least one arcuate fin extending outwardly from the hub ring.

30. The suture package of claim 1 wherein the wheel means comprises three wheels rotatably mounted to the base in the second semicircular end section.

31. A suture package that defines a suture winding channel, comprising
a base having a central area;
a pair of substantially opposed longitudinal walls, and a curved end wall at a first end of the package, said walls extending from the base and said curved end wall connecting said longitudinal walls;
wheel means for assisting dispensing of a suture within the channel from the suture package, said wheel means rotatably connected to the base at a second end opposite said first end of the suture package;
a curved outer wall extending up from the base of the package, the longitudinal walls, curved end wall, the wheel means and curved outer wall defining the suture winding channel;
a suture wound in the suture winding channel
retaining means on the wheel means to retain the suture in the channel, and;
retaining means on the suture winding channel to retain the suture in the channel.

32. The package of claim 31 wherein the retaining means on said suture winding channel comprises a plurality of door means hingingly attached to said suture winding channel, said door means being closable to enclose the suture within said suture winding channel.

33. The package of claim 32 further comprising means for locking said door means in their closed position.

34. The suture package of claim 33, wherein said means for locking said door means comprises a latch mechanism located on said door means and said channel.

35. The suture package of claim 34 wherein said latch means includes an aperture located in said door means and an interlocking post located on said channel.

36. The suture package of claim 35, wherein said door means further includes fin means projecting from said door means for preventing binding of a suture within said latch mechanism.

37. The suture package of claim 32, wherein said suture winding channel is located about the periphery of a central area of said package, said suture winding channel has an open side, and said door means are hingingly attached at said open side of said channel for closure over said open side of said channel along with said wheel means.

38. The suture package of claim 37, wherein said channel further includes an inner wall projecting from the base of said package and standoff means projecting from the inner wall of said channel for bridging sections of said inner wall.

39. The suture package of claim 37, wherein said suture winding channel is located about the periphery of said package and includes an inner wall projecting from the base of said package, and an opposing outer edge, wherein said wheel means comprises a wheel rotatably attached to the base of said package, and wherein said door means are hingingly attached about said outer edge of said channel.

40. The suture package of claim 39, wherein said suture winding channel further includes a curved section extending outward from the base of said inner wall to said outer edge.

41. The suture package of claim 40, wherein said suture winding channel in at least one cross-section comprises a substantially planar inner wall, a planar top wall formed by said door means, and a curved wall connecting said inner and top walls when said door means are closed, wherein portions of said channel are open intermediate said door means when said door means are closed.

42. The suture package of claim 31, wherein said suture winding channel is located about the periphery of said package and includes an inner wall projecting from the base of said package and wherein said suture package further comprises a central area substantially surrounded by said channel and having a point of access to said suture winding channel.

43. The suture package of claim 42, further comprising a needle park means for holding a needle, said needle park means located in said central area and wherein said point of access allows passage of a suture from said central area into said channel.

44. The suture package of claim 43, wherein said point of access is located in the vicinity of the connection of said curved end wall to one of said longitudinal section.

45. The suture package of claim 43, wherein said point of access comprises an opening in the inner wall of said suture winding channel.

46. The suture package of claim 43, further comprising;
a curved needle having a barrel located in said needle park means with the ends of said needle curving away from said point of access; and
the suture attached to the barrel of said curved needle and forming a loop extending from said barrel away from the point of said needle and into said point of access.

47. The suture package of claim 31 further comprising a cover sleeve enclosing said package.

48. The suture package of claim 47, wherein said cover sleeve further includes a scored tear line enabling said cover to preferentially open to reveal a needle location within said package.

49. The package of claim 31 wherein the wheel means comprises at least one wheel rotatably mounted to the base by wheel attachment means for attaching said wheel means to said base.

50. The suture package of claim 49 wherein the at least one wheel comprises a disc having an upper surface and a bottom surface, the disc having an outer ring extending downwardly from the bottom surface of the disc for engaging the suture.

51. The suture package of claim 50 wherein the at least one wheel additionally comprises a second, concentric inner ring extending downwardly from the bottom of the disc for rotatably attaching the at least one wheel to the base, said inner ring having locking means for locking the at least one wheel to the base.

52. The suture package of claim 50 wherein the disc extends outwardly to enclose the end of the suture channel opposite to the curved end wall and adjacent to the wheel.

53. The suture package of claim 50 wherein the at least one wheel comprises a plurality of holes extending through the disc so that the suture contained in the suture package is visible in the channel about the at least one wheel.

54. The suture package of claim 50 wherein said at least one wheel additionally comprises a hole extending through the center of the disc.

55. The suture package of claim 49 wherein the base of the suture channel adjacent to the wheel means is raised.

56. The suture package of claim 49 wherein the wheel attachment means comprises a hub extending upwardly from the base.

57. The suture package of claim 56 wherein the hub comprises a hub ring extending upwardly from the base for rotatably mounting the at least one wheel, said hub having locking means for locking the at least one wheel in place while allowing rotation about the hub.

58. The suture package of claim 57 wherein the locking means comprises at least one arcuate fin extending outwardly from the hub ring.

59. The suture package of claim 31 wherein the wheel means comprises three wheels rotatably mounted to the base in said opposite end.

* * * * *